(12) United States Patent
Tatkov et al.

(10) Patent No.: US 11,464,926 B2
(45) Date of Patent: Oct. 11, 2022

(54) BREATHING CONTROL USING HIGH FLOW RESPIRATION ASSISTANCE

(71) Applicant: Fisher & Paykel Healthcare Limited, Auckland (NZ)

(72) Inventors: Stanislav Tatkov, Auckland (NZ); David Robin Whiting, Auckland (NZ); Jonathan David Harwood, Auckland (NZ)

(73) Assignee: Fisher & Paykel Healthcare Limited, Auckland (NZ)

( * ) Notice: Subject to any disclaimer, the term of this patent is extended or adjusted under 35 U.S.C. 154(b) by 1096 days.

(21) Appl. No.: 14/895,908

(22) PCT Filed: Jun. 5, 2014

(86) PCT No.: PCT/NZ2014/000105
§ 371 (c)(1),
(2) Date: Dec. 3, 2015

(87) PCT Pub. No.: WO2014/196875
PCT Pub. Date: Dec. 11, 2014

(65) Prior Publication Data
US 2016/0121063 A1    May 5, 2016

Related U.S. Application Data

(60) Provisional application No. 61/982,718, filed on Apr. 22, 2014, provisional application No. 61/831,411, filed on Jun. 5, 2013.

(51) Int. Cl.
*A61M 16/00*    (2006.01)
*A61M 16/06*    (2006.01)
(Continued)

(52) U.S. Cl.
CPC ...... *A61M 16/0057* (2013.01); *A61M 16/024* (2017.08); *A61M 16/026* (2017.08);
(Continued)

(58) Field of Classification Search
CPC .... A61M 2230/005; A61M 2202/0007; A61M 2202/0208; A61M 2202/0233;
(Continued)

(56) References Cited

U.S. PATENT DOCUMENTS 7,077,132 B2 * 7/2006 Berthon-Jones ...... A61M 16/00
128/204.18
7,717,110 B2 * 5/2010 Kane ................. A61M 16/0003
128/204.21
(Continued)

FOREIGN PATENT DOCUMENTS

EP    2008581    12/2008
EP    1996265 B1    10/2015
(Continued)

OTHER PUBLICATIONS

International Search Report and Written Opinion for PCT/NZ2014/000105 dated Oct. 20, 2014.
(Continued)

*Primary Examiner* — Michael J Tsai
(74) *Attorney, Agent, or Firm* — Knobbe, Martens, Olson & Bear, LLP

(57) ABSTRACT

High flow therapy is used to treat Cheyne-Stokes respiration and other types of periodic respiration disorders by periodic application of high flow therapy, adjustment of high flow therapy flow rates and/or periodic additions of CO2 or O2 into the air flow provided to the patient.

21 Claims, 13 Drawing Sheets

(51) Int. Cl.
*A61M 16/16* (2006.01)
*A61M 16/20* (2006.01)
*A61M 16/12* (2006.01)

(52) U.S. Cl.
CPC ..... *A61M 16/0045* (2013.01); *A61M 16/0069* (2014.02); *A61M 16/06* (2013.01); *A61M 16/0666* (2013.01); *A61M 16/12* (2013.01); *A61M 16/16* (2013.01); *A61M 16/204* (2014.02); *A61M 2016/0027* (2013.01); *A61M 2016/0033* (2013.01); *A61M 2202/0208* (2013.01); *A61M 2202/0233* (2013.01); *A61M 2205/3334* (2013.01); *A61M 2205/3365* (2013.01); *A61M 2205/3375* (2013.01); *A61M 2205/50* (2013.01); *A61M 2230/005* (2013.01); *A61M 2230/40* (2013.01); *A61M 2230/42* (2013.01)

(58) Field of Classification Search
CPC .......... A61M 2230/40; A61M 2230/42; A61M 16/0045; A61M 16/0057; A61M 16/0069; A61M 16/024; A61M 16/026; A61M 16/06; A61M 16/0666; A61M 16/12; A61M 16/16; A61M 2016/0033; A61M 16/204; A61M 2016/0027; A61M 2205/3334; A61M 2205/3365; A61M 2205/3375; A61M 2205/50
See application file for complete search history.

(56) References Cited

U.S. PATENT DOCUMENTS

| | | | |
|---|---|---|---|
| 8,695,595 B2 | 4/2014 | Kane et al. | |
| 8,794,235 B2* | 8/2014 | Garde | A61M 16/0045 128/204.23 |
| 2001/0035185 A1 | 11/2001 | Christopher | |
| 2002/0088465 A1* | 7/2002 | Hill | A61M 16/026 128/204.23 |
| 2004/0216740 A1 | 11/2004 | Remmers et al. | |
| 2006/0201505 A1* | 9/2006 | Remmers | A61M 16/0045 128/204.21 |
| 2007/0175473 A1* | 8/2007 | Lewis | A61M 16/085 128/204.18 |
| 2008/0223375 A1* | 9/2008 | Cortez | A61M 16/0688 128/207.18 |
| 2008/0302364 A1 | 12/2008 | Garde et al. | |
| 2011/0094518 A1* | 4/2011 | Cipollone | A61M 16/0858 128/207.18 |
| 2011/0214676 A1 | 9/2011 | Allum et al. | |
| 2012/0017904 A1* | 1/2012 | Ratto | A61M 16/0666 128/203.26 |
| 2012/0029321 A1* | 2/2012 | Makaretz | A61M 16/04 600/301 |
| 2012/0055482 A1* | 3/2012 | Wilkinson | A61M 16/024 128/205.25 |
| 2012/0216806 A1* | 8/2012 | Rookard | A61M 16/06 128/203.29 |
| 2012/0251594 A1* | 10/2012 | Longest | A61K 9/008 424/400 |
| 2012/0304993 A1* | 12/2012 | Nitta | A61M 16/0072 128/204.18 |
| 2013/0118494 A1 | 5/2013 | Ujhazy et al. | |
| 2015/0083123 A1* | 3/2015 | Tero | A61M 16/0875 128/202.27 |
| 2017/0049984 A1* | 2/2017 | Biener | A61M 16/0683 |

FOREIGN PATENT DOCUMENTS

| | | |
|---|---|---|
| WO | WO 2005/067520 | 7/2005 |
| WO | WO 2006/039587 | 4/2006 |
| WO | WO 2008/076230 | 6/2008 |
| WO | WO 2008/092021 | 7/2008 |
| WO | WO 2008/154430 | 12/2008 |
| WO | WO 2011/068418 | 6/2011 |
| WO | WO 2012/095813 | 7/2012 |

OTHER PUBLICATIONS

European Search Report for Appl. No. 14807094.9 dated Feb. 16, 2017 in 13 pages.

* cited by examiner

BREATHING CONTROL USING HIGH FLOW RESPIRATION ASSISTANCE

INCORPORATION BY REFERENCE TO ANY PRIORITY APPLICATIONS

The present application is a national phase of PCT Application No. PCT/NZ2014/000105, filed Jun. 5, 2014 titled Breathing Control Using high Flow Respiration Assistance, which claims priority benefit under 35 U.S.C. § 119(e) to U.S. Provisional Patent Application Ser. No. 61/831,411, filed Jun. 5, 2013, titled Breathing Control Using Nasal High Flow and Carbon Dioxide; U.S. Provisional Patent Application Ser. No. 61/982,718, filed Apr. 22, 2014, titled Breathing Control Using High Flow Respiration Assistance; and any and all applications for which a foreign or domestic priority claim is identified in the Application Data Sheet as filed with the present application. Each of the foregoing are hereby incorporated by reference under 37 CFR 1.57.

FIELD OF THE DISCLOSURE

The present disclosure generally relates to high flow breathing therapy. More particularly, the present disclosure relates to controlling a level of residual carbon dioxide within a patient.

BACKGROUND

High flow airway respiratory support delivers a high flow of respiratory gas to a patient. In some configurations, the high flow of respiratory gas can be delivered via a nasal cannula. The supplied respiratory gas can be heated to near body temperature. In some configurations, the supplied respiratory gas can be humidified. In some such configurations, the supplied respiratory gas can be humidified to a saturation point.

In high flow therapy, the respiratory gas is delivered at flow rates that meet or exceed the patient's inspiratory flow rate (for example, in some embodiments, in excess of 12 liters per minute). For some forms of high flow therapy, a source of oxygen can be blended with compressed air. Hospitals usually have 50 psi compressed oxygen and air available for therapeutic use. Accordingly, air can be delivered or an oxygen blender can be used to deliver blends of air and oxygen. The delivered gas can be heated, generally to about 37° C., and can be humidified to near 100% relative humidity (RH) using a humidifier. The gas can be transported to the patient through a heated delivery tube to reduce cooling and condensation of the water vapor that has been added to the respiratory gases.

In some configurations, high flow therapy employs nasal cannulas together with a system designed to deliver high flow rates. In such configurations, the nasal cannula can have a small diameter such that the nasal cannula does not occlude more than about 50% of the nares. By limiting the occlusion of the nares, outward flow can occur during exhalation, which allows end-expiratory $CO_2$ to be flushed from the nasopharyngeal cavity. This also produces resistance to expiration, which increases the length of time for expiration and decreases the respiration rate. With nasal high flow therapy, the clinician can deliver higher $FiO_2$ to the patient than is possible with typical oxygen delivery therapy and without the use of a non-rebreather mask or tracheal intubation.

SUMMARY

The present disclosure describes the use of high flow therapy to assist patients who are suffering from specific respiratory disorders. In an embodiment, the disclosure describes diagnosing a specific breathing disorder and periodically applying high flow therapy in order to treat the breathing disorder. In an embodiment, the breathing disorder is Cheyne-Stokes Respiration (CSR).

In an embodiment, the present disclosure describes making use of varying the delivery of high flow therapy to manipulate the amount of rebreathed $CO_2$. The delivery, adjustment and/or removal of high flow therapy is targeted at specific phases of the CSR cycle or other respiratory disorders. This is designed to manipulate the amount of $CO_2$ in the anatomical dead space of a patient and therefore manipulate the amount of $CO_2$ that is rebreathed during critical times of the CSR cycle or other respiratory disorders. By targeting delivery of high flow therapy during critical phases of the CSR cycle or other respiratory disorder cycles, the fluctuation of $PaCO_2$ at the lungs can be stabilized resulting in normal respiration.

In an embodiment, the present disclosure describes sensing a characteristic of a breathing pattern and initiating a sequence to increase carbon dioxide rebreathing. Increasing carbon dioxide rebreathing can be accomplished by decreasing flow during high flow therapy, capturing expelled $CO_2$ for rebreathing and/or increasing a carbon dioxide content ratio in a breathing gas being supplied to the user.

In an embodiment, a method of treating Cheyne-Stokes Respiration (CSR) is disclosed. The method includes measuring a signal indicative of respiration of a patient, analysing the signal to determine if the signal indicates that the patient is suffering from CSR and applying a high flow therapy to the patient. In an embodiment, the method can include analysing the signal to determine if the signal indicates that the patient is suffering from CSR includes analysing the signal for periods of shallow breathing or apneas in between periods of heavy breathing or hyperventilation. In an embodiment, analysing the signal to determine if the signal indicates that the patient is suffering from CSR includes analysing the signal for periods of a waxing respiration portion and a waning respiration portion. In an embodiment, applying the nasal high flow occurs during a transition between the waxing portion and the waning portion. In an embodiment, the method includes identifying a period and phases of the signal indicative of the respiration of the patient. In an embodiment, initiating the nasal high flow occurs during at least one of the phases. In an embodiment, the method includes identifying a phase delay associated with chemoreceptor signals of the patient. In an embodiment, initiating the nasal high flow incorporates the phase delay. In an embodiment, a periodic signal amplitude having a 90% reduction of a normal signal amplitude is indicative of CSR. In an embodiment, a signal amplitude having an approximately 50% reduction from a normal signal amplitude is indicative of CSR. In an embodiment, the amplitude continues for about 10 seconds or more. In an embodiment, the high flow is about 40 litres per minute. In an embodiment, the method further includes humidifying air used in the high flow therapy. In an embodiment, the high flow therapy is nasal high flow therapy. In an embodiment, the high flow therapy is applied for a window of time less than or approximately equal to the period of the CSR cycle. In an embodiment, measuring is performed by a sensor. In an embodiment, analysing is performed by a hardware processor. In an embodiment, the applying is performed by a high flow respiratory assistance device.

In an embodiment, a system for treating Cheyne-Stokes Respiration (CSR) is disclosed. The system includes a flow source configured to provide a high flow of respiratory gas, a non-sealing interface in fluid communication with the flow source, a sensor configured to sense a breathing amplitude and generate a breathing amplitude signal, and a controller configured to receive the breathing amplitude signal from the sensor, identify respiration indicative of CSR, and control the flow of gas based on the identification of the respiration indicative of CSR. In an embodiment, the system also includes a humidifier in fluid communication with and between the flow source and the interface. In an embodiment, the system performs the method described above.

In an embodiment, a method of treating respiratory disorders using high flow respiratory assistance is disclosed. The method includes identifying a respiratory disorder, determining a transition between a waxing period and a waning period of the respiratory disorder, applying therapeutic high flow therapy, and evaluating the effectiveness of the therapy. In an embodiment, the respiratory disorder is Cheyne-Stokes Respiration. In an embodiment, the therapeutic high flow therapy is nasal high flow therapy. In an embodiment, applying high flow therapy includes applying high flow therapy periodically. In an embodiment, applying the high flow therapy includes applying high flow therapy intermittently. In an embodiment, applying high flow therapy includes applying high flow therapy cyclically. In an embodiment, applying the high flow therapy includes changing a flow rate. In an embodiment, applying the high flow therapy includes using a mixture of air and CO2. In an embodiment, applying high flow therapy includes using a mixture of air and O2. In an embodiment, applying high flow therapy includes using a mixture of air and CO2. In an embodiment, the method is performed using a high flow respiratory assistance device. In an embodiment, the high flow respiratory assistance device is a nasal high flow device. In an embodiment, the high flow respiratory assistance device includes at least one sensor and at least one controller.

In an embodiment, a system which provides respiratory assistance using high flow therapy is disclosed. The system includes a non-sealed mask configured to capture expired $CO_2$, a high flow source configured to provide respiratory gas to a patient through the non-sealed mask, at least one sensor configured to measure a breathing parameter of a patient, and a controller configured to receive information from the sensor indicative of the breathing parameter and determine when to apply the high flow source to the patient through the non-sealed mask. In an embodiment, the high flow source is configured to flush expired CO2 from the non-sealed mask. In an embodiment, the high flow source is configured to flush expired CO2 from respiratory dead space of the patient.

In an embodiment, a method of treating a respiratory disorder is disclosed. The method includes determining a phase delay procedure for applying high flow therapy to treat a respiratory disorder and applying high flow therapy according to the phase delay procedure. In an embodiment, the method also includes evaluating an effectiveness of the high flow therapy. In an embodiment, evaluating the effectiveness includes determining if the respiratory disorder has improved. In an embodiment, the method also includes adjusting the phase delay procedure based on the evaluation. In an embodiment, a phase delay of the phase delay procedure is increased over time. In an embodiment, a phase delay of the phase delay procedure is decreased over time. In an embodiment, a phase delay of the phase delay procedure is phased in over a period of time. In an embodiment, the period of time is one of an hour, night, session or set of sessions. In an embodiment, the respiratory disorder is Cheyne-Stokes breathing. In an embodiment, a phase delay of the phase delay procedure is a time delay from the detection of a decrease or increase in tidal flow of breathing of the patient to an increase or decrease in a flow of gases delivered to an interface of the patient. In an embodiment, a magnitude of a flow of gases delivered to a patient is oscillated. In an embodiment, the oscillation is based on a period of oscillation of breathing of the patient. In an embodiment, the oscillation tracks the shape of the oscillatory breathing of the patient. In an embodiment, a peak flow delivered to the patient may be adjusted using a scaling factor based on a difference between a maximum and minimum patient breathing tidal flow. In an embodiment, the scaling factor is constant. In an embodiment, a phase delay of the phase delay procedure varies between zero degrees and three hundred and sixty degrees. In an embodiment, a phase delay of the phase delay procedure varies between zero and one hundred and eighty degrees. In an embodiment, a phase delay of the phase delay procedure varies between zero and forty five degrees.

In an embodiment, a system configured to treat a respiratory disorder is disclosed. The system includes a sensor configured to determine an indication of a respiratory pattern of a patient, a hardware controller configured to receive the indication of the respiratory pattern of the patient and determine a phase delay procedure for applying high flow therapy to treat a respiratory disorder, and a flow generator, controlled by the hardware controller, the flow generator configured to provide a high flow therapy to the patient, wherein the hardware controller controls the flow generator to provide a high flow therapy according to the determined phase delay procedure. In an embodiment, the hardware controller is further configured to evaluate an effectiveness of the high flow therapy. In an embodiment, evaluating the effectiveness includes determining if the respiratory disorder has improved. In an embodiment, the hardware controller is further configured to adjust the phase delay procedure based on the evaluation. In an embodiment, a phase delay of the phase delay procedure is increased over time. In an embodiment, a phase delay of the phase delay procedure is decreased over time. In an embodiment, a phase delay of the phase delay procedure is phased in over a period of time. In an embodiment, the period of time is one of an hour, night, session or set of sessions. In an embodiment, the respiratory disorder is Cheyne Stokes breathing. In an embodiment, a phase delay of the phase delay procedure is a time delay from a detection of a decrease or increase in tidal flow of breathing of the patient to an increase or decrease in a flow of gases delivered to an interface of the patient. In an embodiment, a magnitude of a flow of gases delivered to the patient is oscillated. In an embodiment, the oscillation is based on a period of oscillation of the patient's breathing. In an embodiment, the oscillation tracks the shape of the oscillatory breathing of the patient. In an embodiment, a peak flow delivered to the patient may be adjusted using a scaling factor based on a difference between a maximum and minimum patient breathing tidal flow. In an embodiment, the scaling factor is constant. In an embodiment, a phase delay of the phase delay procedure varies between zero degrees and three hundred and sixty degrees. In an embodiment, a phase delay of the phase delay procedure varies between zero and one hundred and eighty degrees. In an embodiment, a phase delay of the phase delay procedure varies between zero and forty five degrees.

BRIEF DESCRIPTION OF THE DRAWINGS

These and other features, aspects and advantages of the present disclosure will be described with respect to the following figures.

DETAILED DESCRIPTION

Respiration is believed to be regulated by central chemoreceptors in the brain, peripheral chemoreceptors in the aortic and carotid body (located in the heart and neck respectively) and mechanoreceptors located throughout the body. The peripheral chemoreceptors are believed to respond to both oxygen ($O_2$) and carbon dioxide ($CO_2$) partial pressures whereas the central chemoreceptors are believed to respond only to $CO_2$ partial pressures. The partial pressure of carbon dioxide ($PaCO_2$) is tightly controlled as it is linked to acidity (pH) in the human body, which needs to be maintained at a constant level for proper organ function. Pulmonary ventilation varies linearly with increases in $PaCO_2$ but it is not until $PaO_2$ is reduced to below 60 mmHg (approximately 88% $SaO_2$) that ventilation is significantly stimulated as a response to prevent hypoxia. This is consistent with the oxygen-hemoglobin dissociation curve which, due to its sigmoid shape, illustrates that the increase of oxyhemoglobin saturation with an increase of $PaO_2$ is relatively small above a $PaO_2$ of approximately 60 mmHg. Below the 60 mmHg threshold oxyhemoglobin saturation changes much more significantly with changes in $PaO_2$.

Figure 1A:
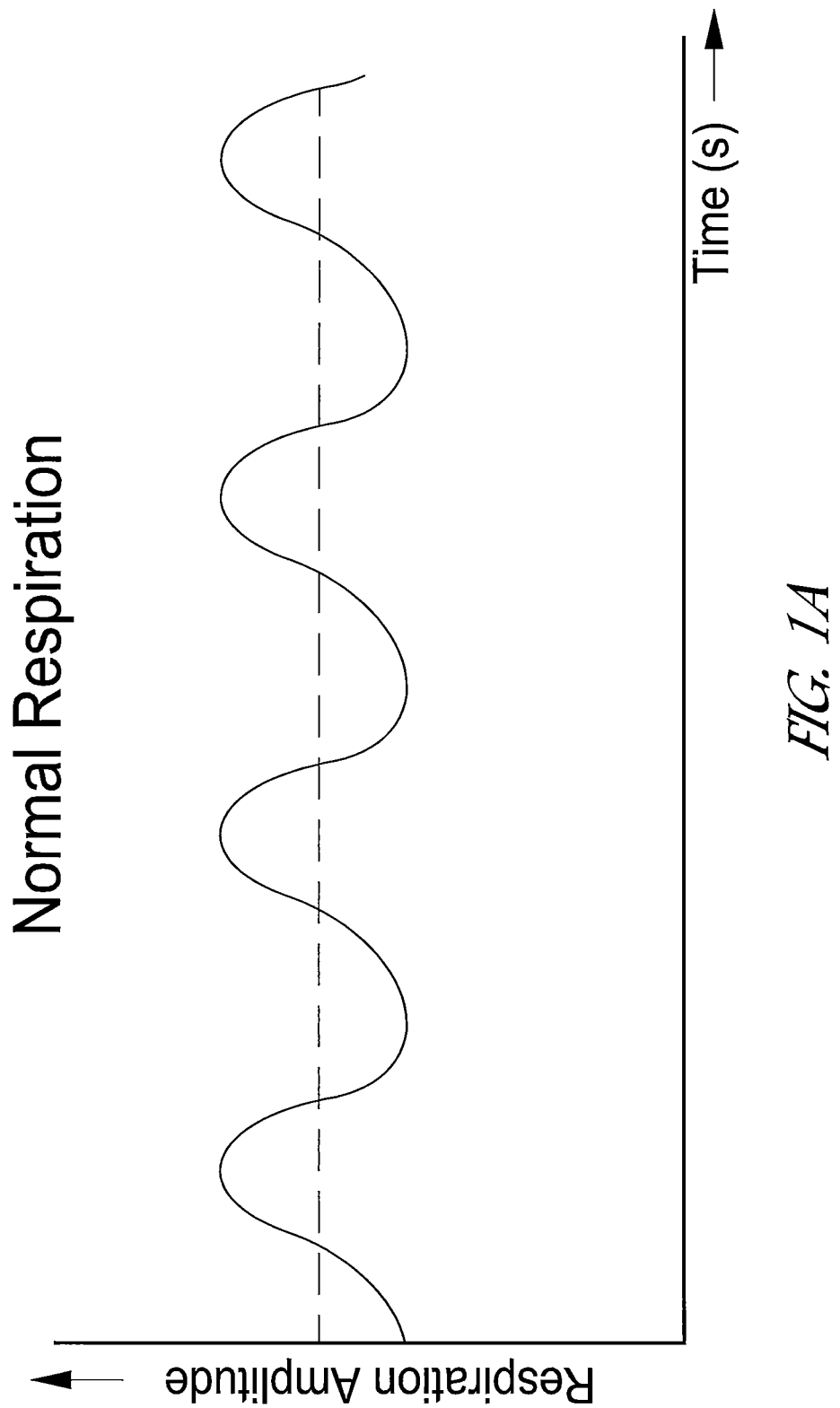
FIG. 1A is a graph illustrating a flow signal of normal respiration.

The complete respiratory control system is complex and depending on how the system is viewed, any number of congestive heart failure (CHF) related consequences can lead to oscillations of ventilation, especially when combined with sleep/wake transitions due to arousals. A simple model that can lead to periodic breathing is based around changes in ventilation between the sleep and awake states. When a healthy person enters NREM sleep, there is a reduction in central respiratory drive, a loss of nonchemical wakefulness drive, and metabolic control dominates. These factors typically result in a decreased minute ventilation and an increased $PaCO_2$. As long as $PaCO_2$ remains greater than the apneic threshold (defined as the level of $PaCO_2$ below which rhythmic breathing ceases) rhythmic breathing continues. A flow signal representing a normal or healthy breathing pattern is illustrated in FIG. 1A. Some patients, however, particularly those with CHF, tend not to increase their $PaCO_2$ upon entering sleep resulting in a $PaCO_2$ close to the apneic threshold, predisposing them to central apnea. Consider a hypocapnic CHF patient. When the patient enters sleep, if the patient's $PaCO_2$ does not rise and is below the hypocapnic apnea threshold, ventilation ceases and an apnea results. The apnea produces an increase in $PaCO_2$ and a decrease in $PaO_2$ sufficient to force the respiratory drive past the arousal threshold and the patient wakes from sleep. The arousal results in hyperventilation due to the reinstitution of the nonchemical waking drive and increased chemical drive to breath. The patient then returns to sleep and the cycle repeats. This type of apnea/hyperventilation respiration cycle is referred to as Cheyne-Stokes Respiration (CSR).

FIG. 1A illustrates a flow signal indicative of Cheyne-Stokes respiration. CSR is characterized by a waxing period of progressively deeper and sometimes faster breathing or hyperventilation, followed by a waning period having a gradual decrease that results in very shallow breaths that may include hypopneas or apneas. The pattern repeats, with each cycle usually taking 30 seconds to 2 minutes. The pattern, therefore, can be considered an oscillation of ventilation between apnea or hypopnea and hyperventilation with a crescendo-decrescendo ventilation pattern. As described above, CSR is generally associated with changing serum partial pressures of oxygen and carbon dioxide.

Figure 1B:
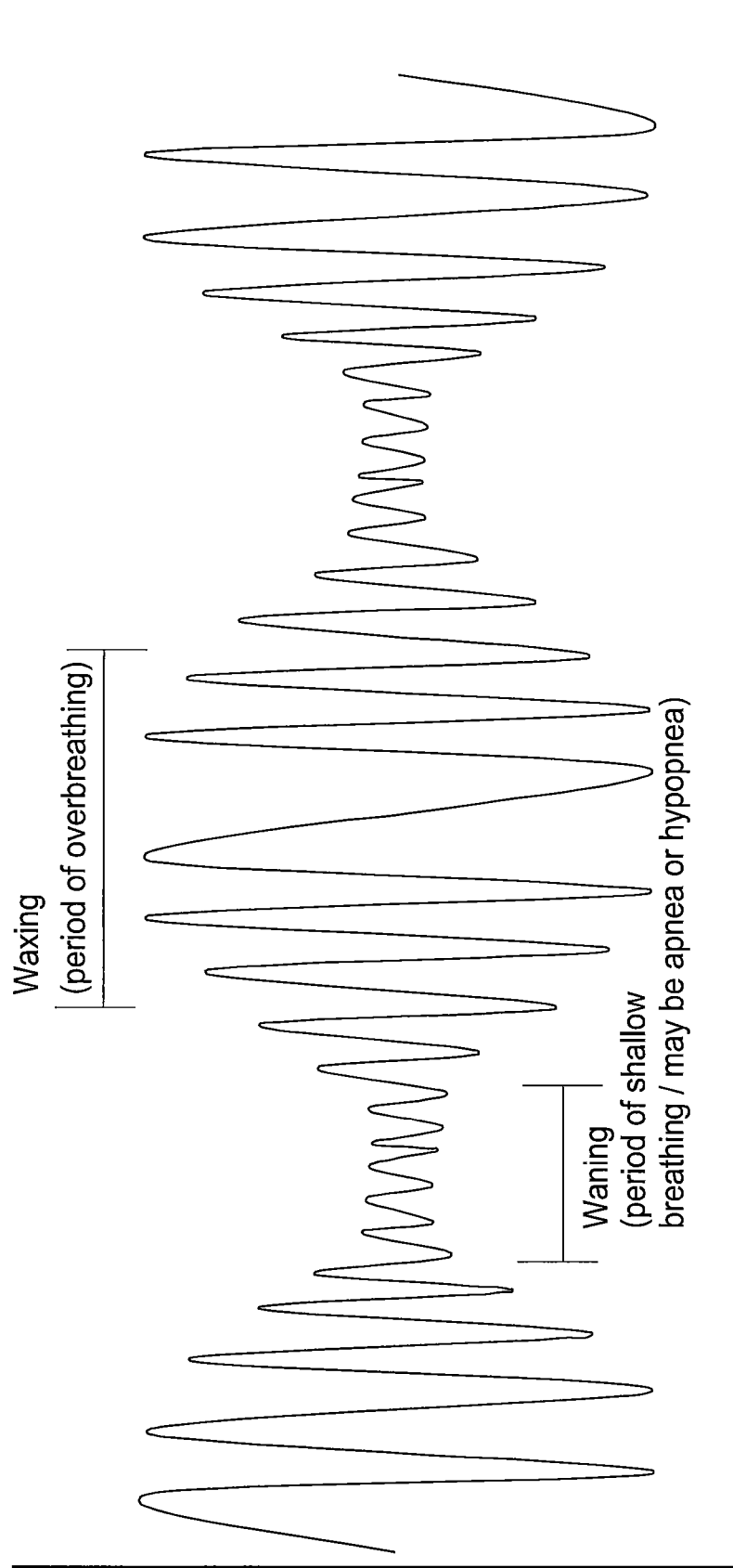
FIG. 1B is a graph illustrating a flow signal of Cheyne-Stokes Respiration.

Cheyne-Stokes breathing has been recognized to occur in a high percentage of patients suffering from CHF. The pathophysiology of Cheyne-Stokes breathing can be summarized as apnea leading to increased carbon dioxide, which causes excessive compensatory hyperventilation, in turn causing decreased carbon dioxide, which causes apnea, restarting the cycle. A graphical illustration of such a breathing pattern can be found in the diagrams of FIG. 1B.

More complex models can use control system theory to model the respiratory system as a feedback control system and to make predictions regarding the appearance of Cheyne-Stokes respiration. Linear stability analysis shows that a system with a high loop gain will result in Cheyne-Stokes type breathing. The response to transient changes in ventilation are inappropriately magnified due to an abnormally increased loop gain, potentially as a result of increased chemoreceptor sensitivity, low functional residual capacity or other factors. The result of this inappropriate response is oscillations in the minute ventilation by under and overshooting the equilibrium point.

Figure 2:
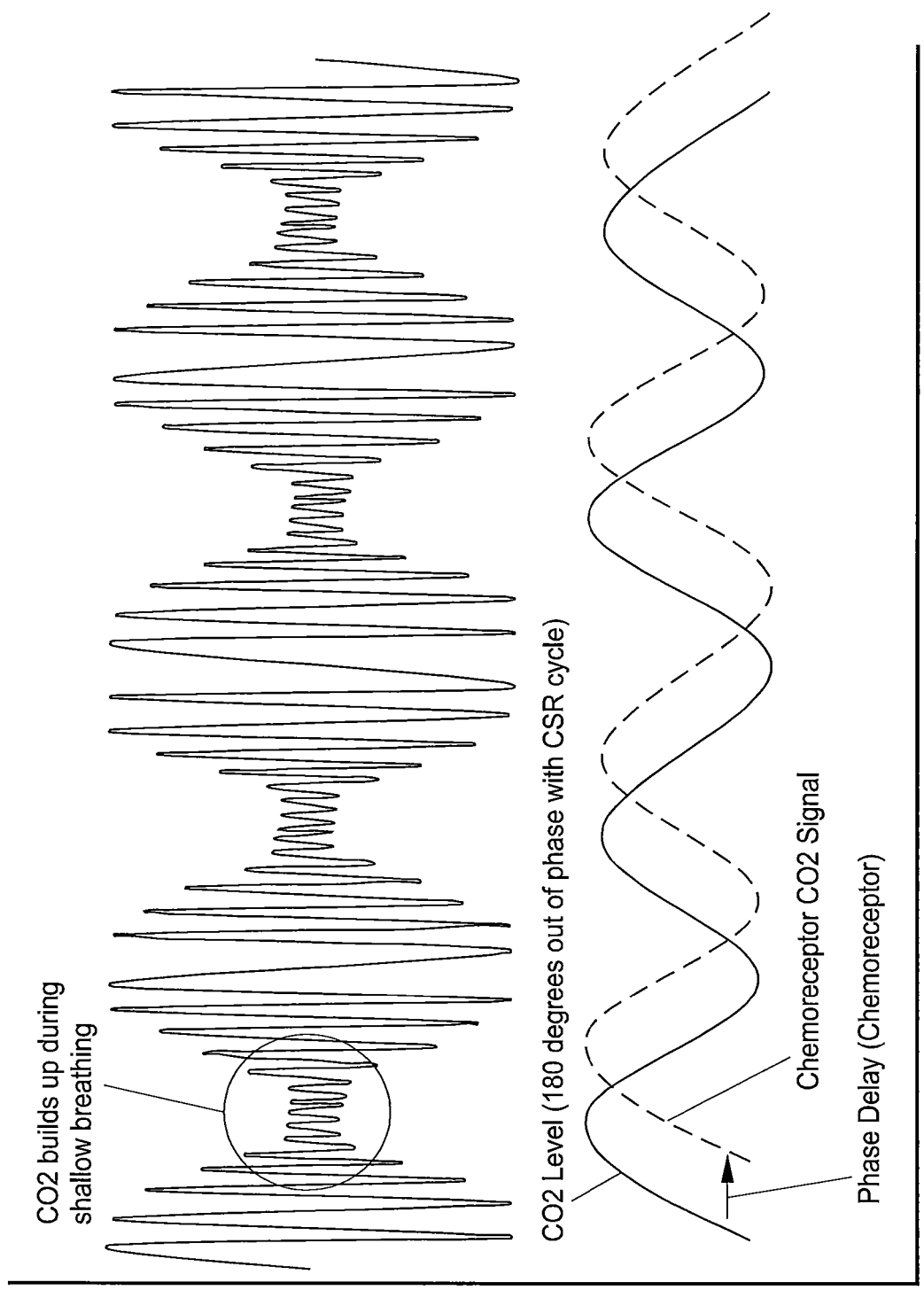
FIG. 2 illustrates a graph of the phase delay of sensing $CO_2$ levels associated with a patient's chemoreceptors associated with Cheyne-Stokes Respiration.

Time delays in the system also promote instability. Time delays in the system promote oscillation via "hunting" type behavior and can ultimately result in a negative feedback system behaving as a positive feedback system which is equivalent to the high loop gain system discussed above. In CHF patients increased circulation time, due to reduced cardiac output, increases time delays between changes in ventilation and detection of $PaCO_2$ and $PaO_2$ by chemoreceptors and hence can promote Cheyne-Stokes Respiration (CSR). As shown in FIG. 2, $PaCO_2$ levels at the lungs rise and fall out of phase with the waxing and waning cycles indicative of CSR. Although PaCO2 levels at the lungs will be out of phase with the breathing pattern, $PaCO_2$ levels at the chemoreceptors will have an additional phase delay by as much as or more than 180 degrees with the waxing and waning cycles. The additional phase delay is caused by the time it takes the blood from the lungs to reach the central (brain) chemoreceptor and the peripheral (neck) chemoreceptors.

As an example of how excessively high loop gain can cause breathing instabilities, consider a sleeping patient that has a need to reduce their ventilation. The control system's excessively high loop gain does not cause a gradual reduction in ventilation, but rather causes a more rapid decrease in ventilation which results in an overshooting of $PaCO_2$ above the desired set point. As $PaCO_2$ has overshot its required target, ventilation increases and the cycle either repeats indefinitely or the patient wakes up resetting the system. This is in contrast to a system with a normal loop gain which, assuming the patient doesn't wake up, would result in the oscillations damping out towards a stable equilibrium point.

More complex models of respiration can use non-linear dynamical models and the mathematical theory of bifurcations to predict the presence of Hopf bifurcations and limit cycles. If a Hopf bifurcation exists in a system, a stable steady state point of a system can potentially evolve into a stable oscillating limit cycle and vice versa. Using this concept CSR can spontaneously appear and disappear given a transient change in lung volume, ventilation-perfusion ratio, feedback control gain, transport delay, left heart volume, lung congestion or cardiovascular efficiency.

Figure 3:
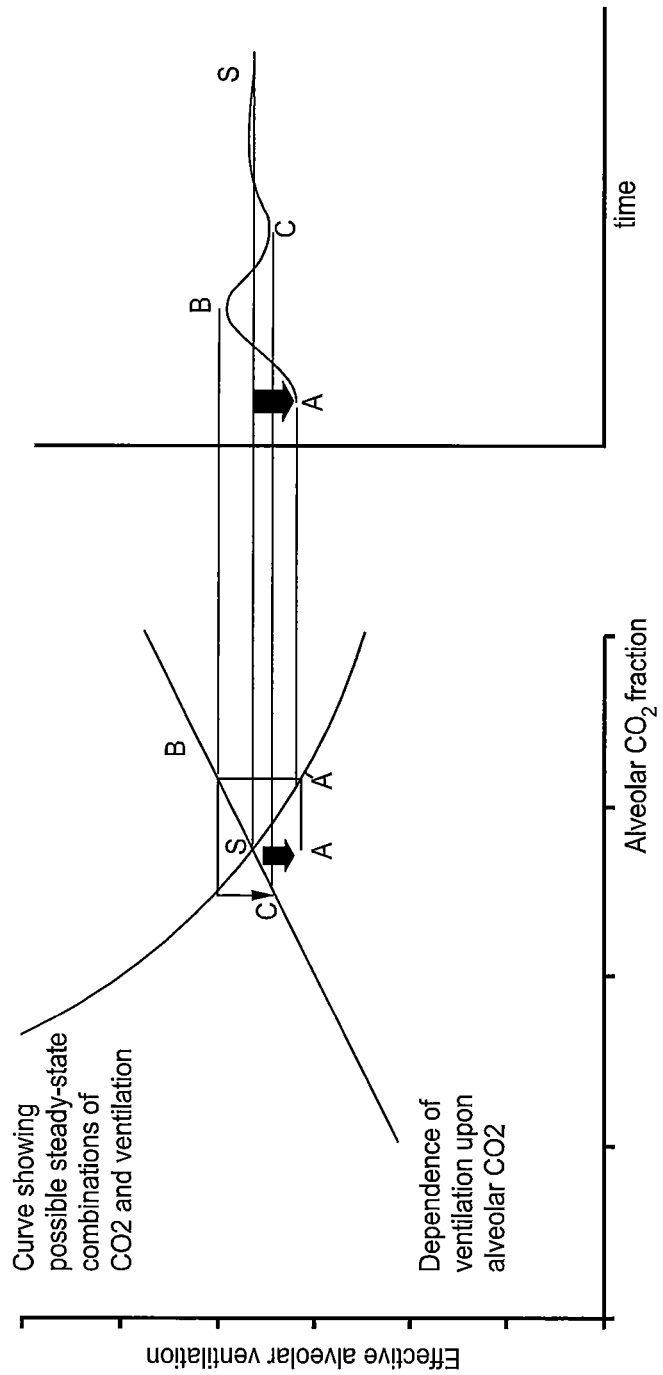
FIG. 3 is a graphical depiction of steady state combinations of carbon dioxide and ventilation.

As mentioned above, in normal respiratory control, negative feedback based on $PaCO_2$ levels allows a steady level of alveolar gas concentrations to be maintained. Therefore, stable tissue levels of oxygen and carbon dioxide exist. At steady state, the rate of production of carbon dioxide equals the net rate at which it is exhaled from the body, which (assuming no carbon dioxide in the ambient air) is the product of the alveolar ventilation and the end-tidal carbon dioxide concentration. Because of this interrelationship, the set of possible steady states forms a hyperbola as shown in FIG. 3: Alveolar ventilation=body $CO_2$ production/end-tidal $CO_2$ fraction.

In FIG. 3, this relationship is the curve falling from the top left to the bottom right. Only positions along this curve permit the body's carbon dioxide production to be exactly compensated for by exhalation of carbon dioxide. Meanwhile, there is another curve, shown in the figure for simplicity as a straight line from bottom left to top right, which is the body's ventilatory response to different levels of carbon dioxide. Where the curves cross is a potential steady state (S).

Through respiratory control reflexes, any small transient fall in ventilation (A) leads to a corresponding small rise (A') in alveolar carbon dioxide concentration, which is sensed by the respiratory control system so that there is a subsequent small compensatory rise in ventilation (B) above its steady state level (S) that helps restore carbon dioxide back to its steady state value. In general, transient or persistent disturbances in ventilation, carbon dioxide or oxygen levels can be counteracted by the respiratory control system in this way.

Figure 4:
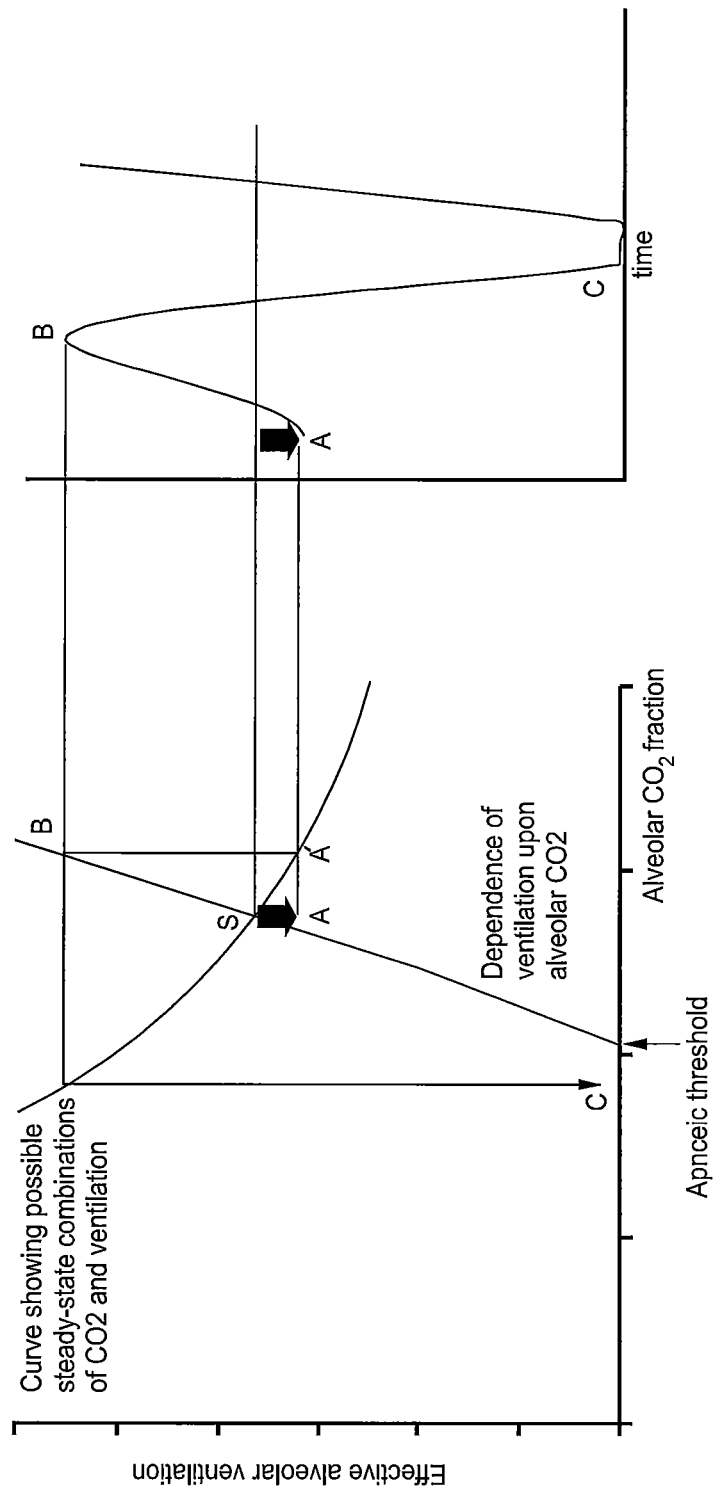
FIG. 4 is another graphical depiction of steady state combinations of carbon dioxide and ventilation.

However, as discussed above, in some pathological states, the feedback is more powerful than is necessary to simply return the system towards its steady state. Instead, ventilation overshoots and can generate an opposite disturbance to the original disturbance. If this secondary disturbance is larger than the original, the next response will be even larger, and so on, until very large oscillations have developed, as shown in FIG. 4.

The cycle of enlargement of disturbances reaches a limit when successive disturbances are no longer larger, which occurs when physiological responses no longer increase linearly in relation to the size of the stimulus. The most obvious example of this is when ventilation falls to zero—it cannot be any lower. Thus Cheyne-Stokes respiration can be maintained over periods of many minutes or hours with a repetitive pattern of waxing and waning respiration.

The end of the linear decrease in ventilation in response to falls in carbon dioxide is not, however, at apnea. The end occurs when ventilation is so small that air being breathed in never reaches the alveolar space because the inspired tidal volume is no larger than the volume of the large airways, such as the trachea. Consequently, at the nadir of periodic breathing, ventilation of the alveolar space may be effectively zero; the easily-observable counterpart of this is failure at that time point of the end-tidal gas concentrations to resemble realistic alveolar concentrations.

Based upon an understanding of the body's reaction to carbon dioxide concentration, it is desired to integrate into a breathing apparatus an algorithm and method for delivering a high flow of respiratory gases while also providing the capability to control breathing either by entrainment of respiratory gas containing carbon dioxide and/or by varying of carbon dioxide re-breathing from anatomical or apparatus dead space. Breathing or re-breathing of carbon dioxide causes the patient to respond with deeper breathing, which helps control an overall breathing profile. In some configurations, certain features, aspects and advantages of the development can be used in periodic types of respiration, such as Cheyne-Stokes, in central sleep apnea and in other forms of disturbances of breathing. In some configurations, if a shallower breath pattern is being detected, then the patient can be encouraged to take a deeper breath by temporarily increasing the level of carbon dioxide rebreathing.

In general, high flow treatment clears anatomical dead space and can be used to control breathing. High flow therapy is usually a non-sealed or open system, allowing excess air to be vented to out to the ambient air, rather than forced into the patient. One type of high flow treatment is nasal high flow treatment. The flow can range from less than about 1 liter per minute to as much or more than about 100 liters per minute. In an embodiment, the flow can be about 40 liters per minute. One range of flows can be about 10 liters per minute to about 40 liters per minute. The high flow of gas can be used, for example, to flush expired or residual $CO_2$ from anatomical dead spaces of a patient. This process helps to reduce or substantially eliminate residual $CO_2$ in a patient's respiratory system. This reduction in residual $CO_2$ in nasal cavity dead space increases ventilation efficiency by increasing the amount of oxygen reaching the lungs in a given breath. One commercially available example of a high flow nasal therapy device is the Airvo™ commercially available from Fisher and Paykel Healthcare of Auckland, NZ.

Figure 5:
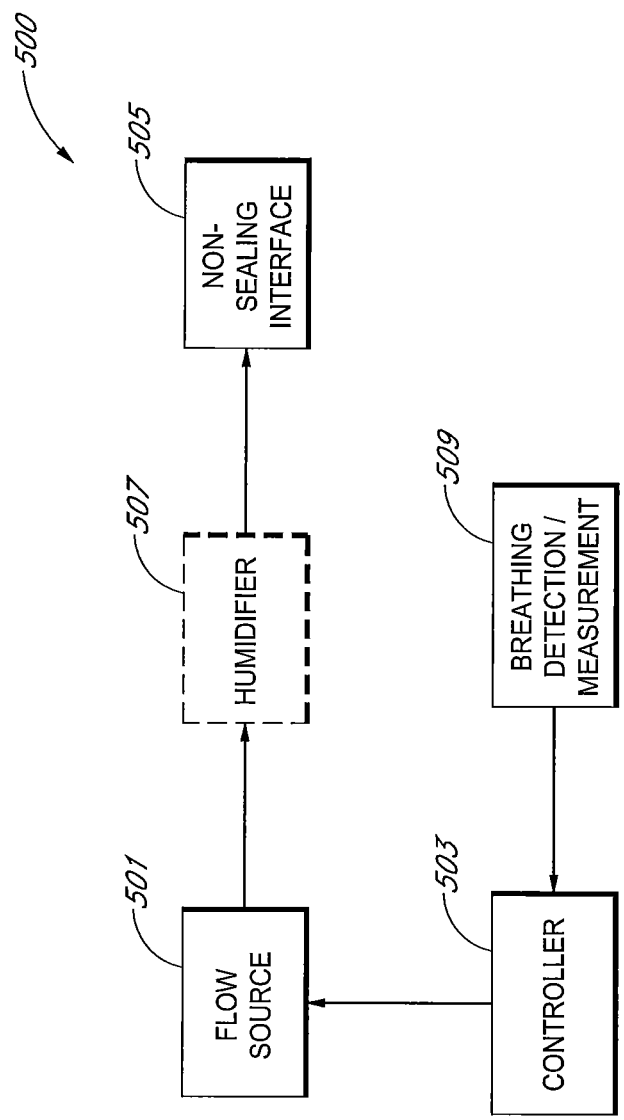
FIG. 5 is a hardware diagram of an embodiment of a high flow respiration therapy system.

FIG. 5 illustrates an embodiment of a system 500 suitable for high flow therapy. The high flow therapy system of FIG. 5 includes a flow source 501 such as, for example, a blower, a generator, a hospital source, or other high flow air source. The system includes a controller 503 for controlling the flow source. For example, this can be a processor or other electrical and/or mechanical system which controls the flow source. The controller can provide a variable speed, a variable setting blower, or valve system to control how and/or when flow is applied. In an embodiment, the system includes a non-sealing interface 505, such as, for example, a nasal cannula in fluid communication with the flow source to direct the flow source into the patient's respiratory system. Optionally, in some embodiments, the system can include a humidifier 507 in fluid communication with the flow source and the interface. The humidifier humidifies the air before it is provided to the patient in order to provide greater comfort and assistance to the patient. The system also includes at least one sensor or detection mechanism 509 for determining the respiration of the patient and/or changes in air flow. This can be a flow sensor, a pressure sensor or a determination based on the motor speed of the flow source. In some embodiments, an abdominal and/or thoracic band(s) can be used with the system to provide information on the patient's respiration. Other sensors can include visual or acoustic measurements including optics, such as lasers, or piezoelectric acoustic sensors.

The controller is configured to manage the operation of the flow source by receiving feedback from the sensor indicative of the flow of the system and/or respiration of the patient. The controller can be configured to identify or detect a CSR pattern or other abnormal breathing pattern and control the operation of the flow source to compensate for the abnormal breathing. The purpose of the control operation is to aid the patient in returning to a normal breathing pattern by regulating the high flow source in such a way that the patient's body regulates itself back to a normal breathing pattern. This can be done by timing an initiation of a flow source, adjustment a flow rate of a flow source or the stopping a flow source. The application of the flow source to assist the patient is described in greater detail below.

Variable high flow, and in particular, nasal high flow, is described, for example, PCT Application No. PCT/NZ2014/000041 filed Mar. 14, 2014 and hereby incorporated by reference in its entirety. Variable high flow can be focused on the dead space clearance and can be controlled in order to stabilize breathing in such conditions as periodic Cheyne-Stokes respiration by increasing or decreasing dead space clearance and/or entrainment of carbon dioxide and/or oxygen to the breathing gas. The dead space clearance of high flow therapy is illustrated below in FIGS. 6A and 6B. In some configurations, flow can be turned on or off at different periods of inspiration or expiration. Similarly, the flow can be increased or decreased or the inspiratory and/or expiratory profile of flow can be altered to control dead space clearance from upper airways of a patient.

Nasal high flow can be delivered either itself or with a hybrid mask interface, such as those described in WO2011/078703, filed Dec. 22, 2010, which claims priority to U.S. Provisional Patent Application No. 61/289,544, filed Dec. 23, 2009, each of which is hereby incorporated by reference in its entirety, or in a combination of nasal prongs with a non-sealed mask, nasal pillow or hood to increase apparatus dead space when nasal flow is decreased. An increase of flow can increase dead space clearance and can reduce carbon dioxide re-breathing while a decrease of flow can increase re-breathing of carbon dioxide.

Figure 6A:
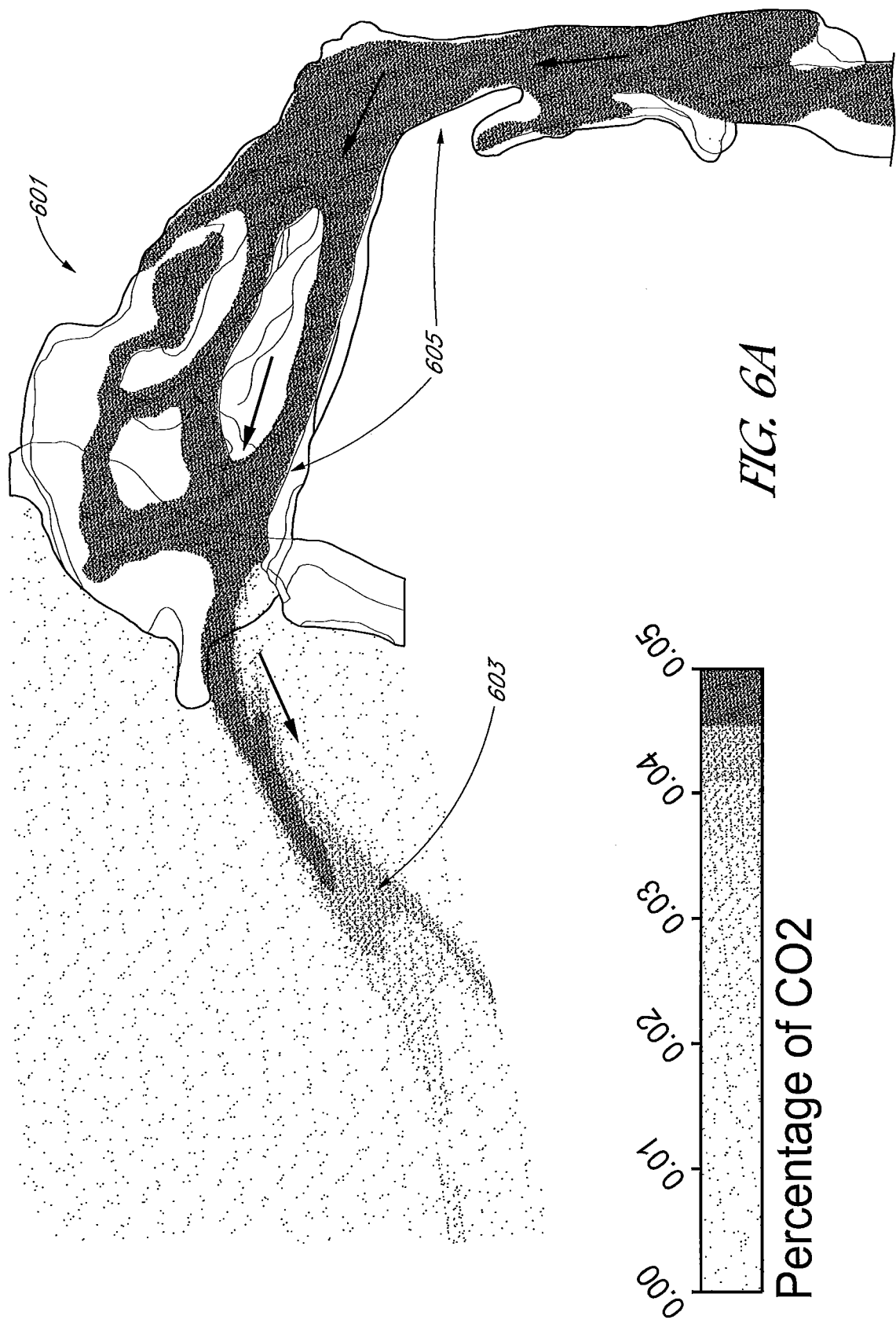
FIG. 6A illustrates a residual $CO_2$ levels in a cross section of dead space within a patient's respiration pathways during normal unaided respiration.
Figure 6B:
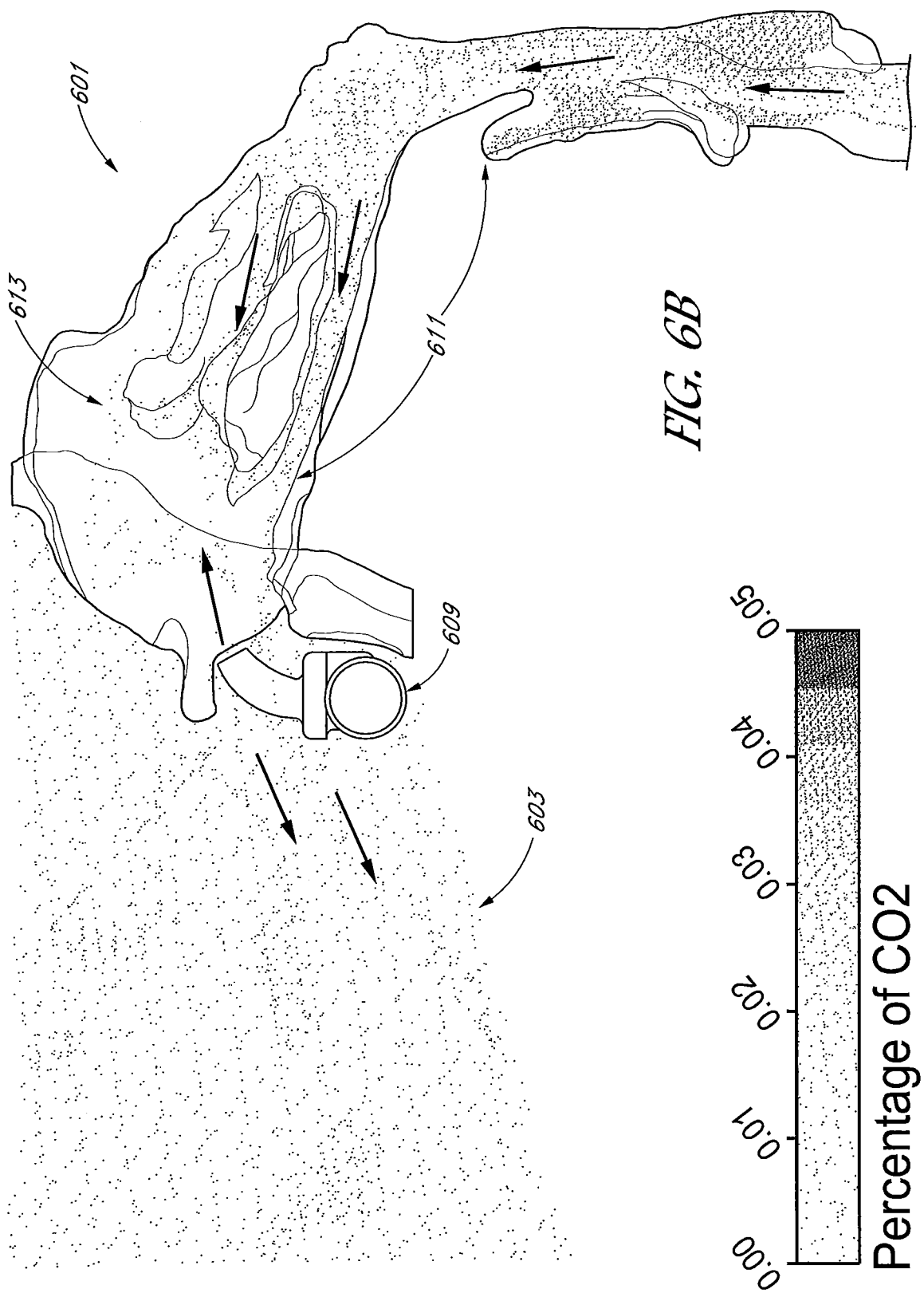
FIG. 6B illustrates a residual $CO_2$ levels in a cross section of dead space within a patient's respiration pathways while using high flow therapy.

FIG. 6A illustrates a cross section of a respiratory tract, including dead space cavities 601. As the patient breaths out, expiration 603 leaves the respiration system, however, residual expiration 605 is left in the cavities. The residual expiration 605 is shown in dark grey to illustrate a relatively high $CO_2$ content. The residual expiration 605 is then sucked back into the lungs with the next inspiration. This results in a higher $CO_2$ concentration and a lower $O_2$ concentration than might be found in the ambient air. FIG. 6B illustrates the same cross section of anatomical space as FIG. 6A, however, FIG. 6B illustrates the effect of nasal high flow therapy during the same point in the respiration cycle. High flow nasal cannula 609 provides nasal high flow therapy to the patient illustrated. As the patient exhales, expired gas 603 is still pushed to the ambient air. However, the high flow cannula 609 provides a flow of air into the respiratory system of the patient. As can be seen in FIG. 6B, this results in a lower overall CO2 concentration in at least a portion of the dead space. For example, at locations 611, the air in the dead space cavities has a generally light color to indicate a lower $CO_2$ content. Although some higher $CO_2$ content air is still residual, for example at 613, the overall $CO_2$ level of the residual air is lower. This leads to an overall higher $O_2$ concentration on the next inspired breath of the patient.

The high flow therapy device can be configured to stabilize CSR by transiently supplying high flow during a cycle of periodic breathing. As discussed above, it is believed that carotid chemoreceptors are sensitive, fast-responding $CO_2$ sensors and it is believed they are important in the initiation of apnea in response to a single ventilatory overshoot. The response to changes in $PaCO_2$ by the carotid chemoreceptors are magnified in the presence of hypoxia. It is thought that the contribution of peripheral chemosensitivity to increases in ventilation is about 25% in normoxia and about 70% in hypoxia (SaO2=75%). During the hypopnea phase of CSR, $PaO_2$ decreases and $PaCO_2$ increases. The decrease in $PaO_2$ increases the respiratory systems response to the increase in $PaCO_2$ and hence encourages hyperventilation which ultimately forms CSR. By supplying high flow therapy during periods of hypopnea, the drop in $PaO_2$ is potentially reduced and hence may provide a stabilizing effect.

High flow therapy also increases Functional Residual Capacity (FRC) via low levels of Positive End Expiratory Pressure (PEEP) which increases oxygen and $CO_2$ stores. This decreases loop gain and hence also potentially helps to stabilize respiration. By turning the device off during periods of hyperventilation the added inspiratory resistance can help to damp the hyperventilation. Finally, by reducing anatomical dead-space through high flow therapy, changes in ventilation will more rapidly result in changes in $PaCO_2$ and $PaO_2$. This is analogous to decreasing delays in the system which may also promote stable breathing.

Thus, in an embodiment of the present system, CSR is treated by, for example, (1) reducing the amount of hypoxia and reducing the potential buildup of $PaCO_2$ during a period of hypoventilation, and therefore reducing the likely of a ventilatory overshoot post hypopnea; (2) increasing FRC, which increases oxygen and $CO_2$ stores, which has a stabilizing effect on respiration; (3) adding nasal resistance during periods of hyperventilation to dampen the hyperventilation; and (4) reducing anatomical dead-space through high flow therapy, which potentially reduces the delays in how ventilation affects $PaCO_2$ and $PaO_2$.

Figure 7:
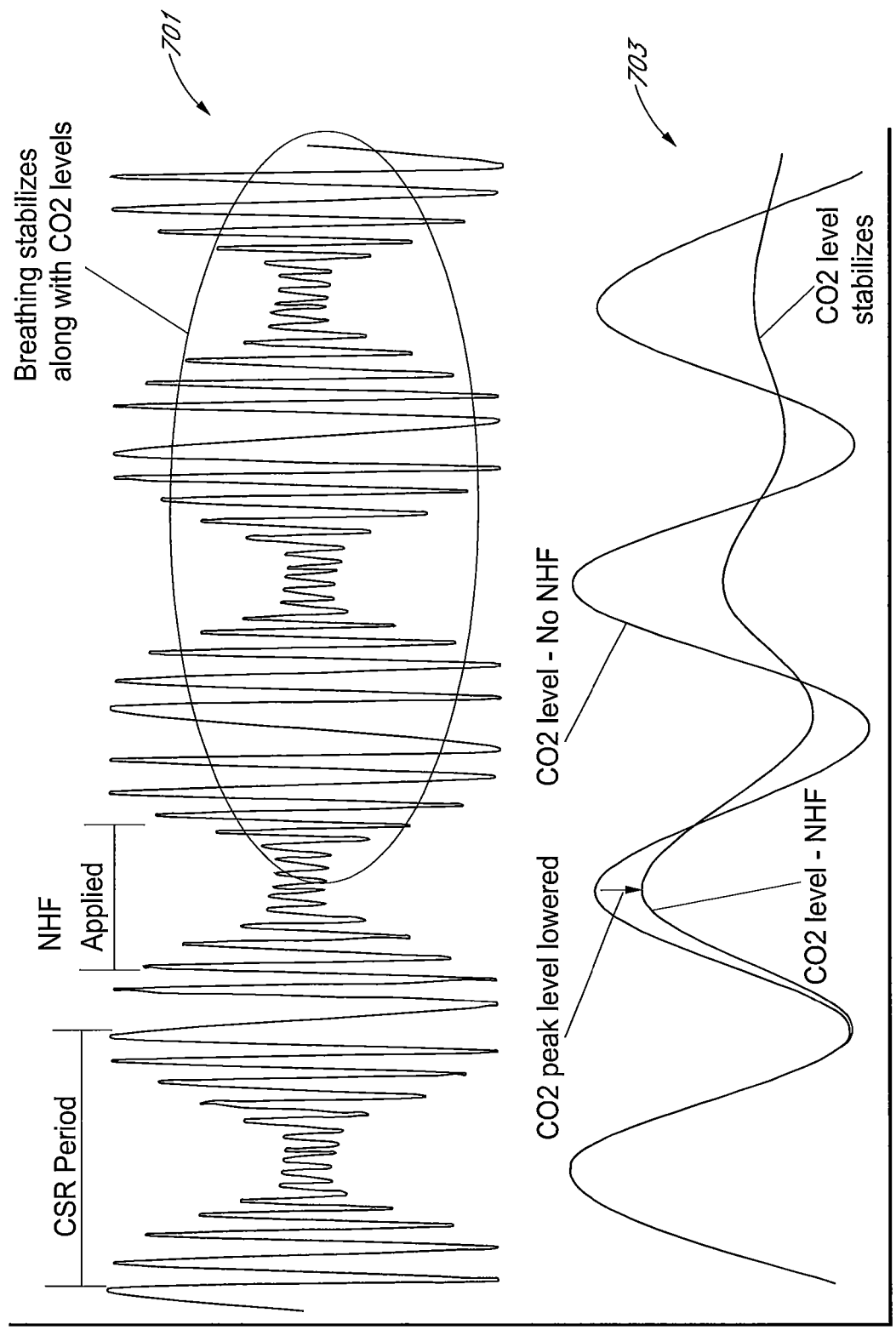
FIG. 7 illustrates graphs indicating the periodic application of high flow therapy and its resulting effects on $CO_2$ levels in the body.

With reference to FIG. 7, a period of CSR cycles is shown on waveform 701. Once appropriately identified, a high flow therapy (for example nasal high flow therapy, "NHF") can be periodically applied in order to dampen the CSR cycle. Upon application of the high flow therapy, the $CO_2$ build-up is limited, as shown in waveform 703, resulting in stabilized $CO_2$ levels which will eventually lead to stabilized breathing.

Figure 8:
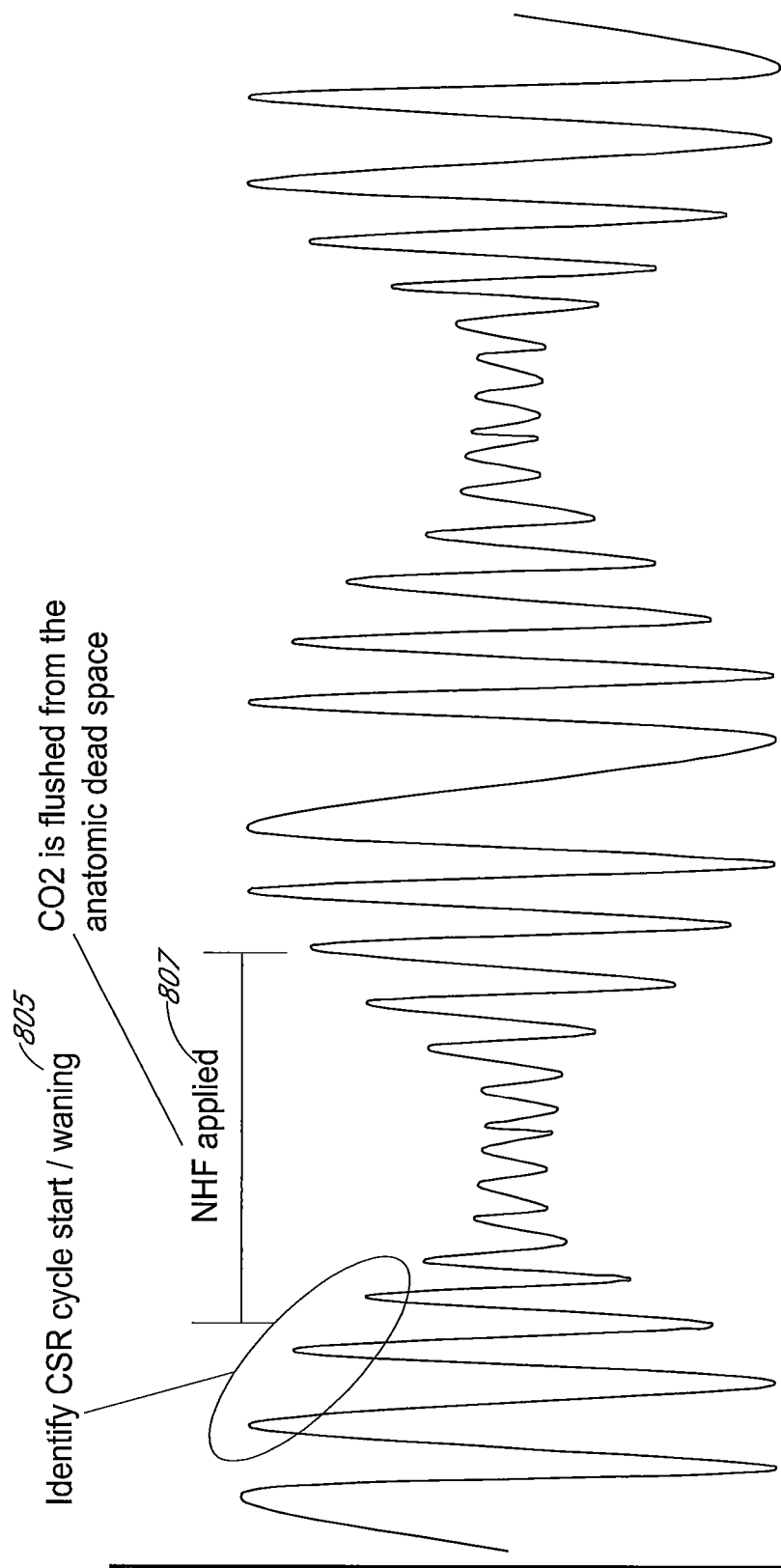
FIG. 8 illustrates another embodiment of the periodic application of high flow therapy.

With reference to FIG. 8, a transition between waxing and waning cycles is determined (indicated as area 805) and high flow therapy (for example nasal high flow therapy, "NHF") is applied during this transition period. In various embodiments, high flow therapy may stop after respiration amplitude begins to increase, for example, during the waxing transition of the CSR cycle. Alternatively, high flow therapy can continue for a predetermined period of time, for example, as indicated during time 807 in FIG. 8. In additional embodiments, the period of high flow therapy is variable, based on, for example, the period of the CSR cycle or other attributes of respiration indicative of CSR. In another example, an average breath volume or minute ventilation is calculated over a period of time and high flow therapy is applied during breaths that are below this threshold. In an embodiment, high flow therapy is applied only during exhalation.

Figure 9:
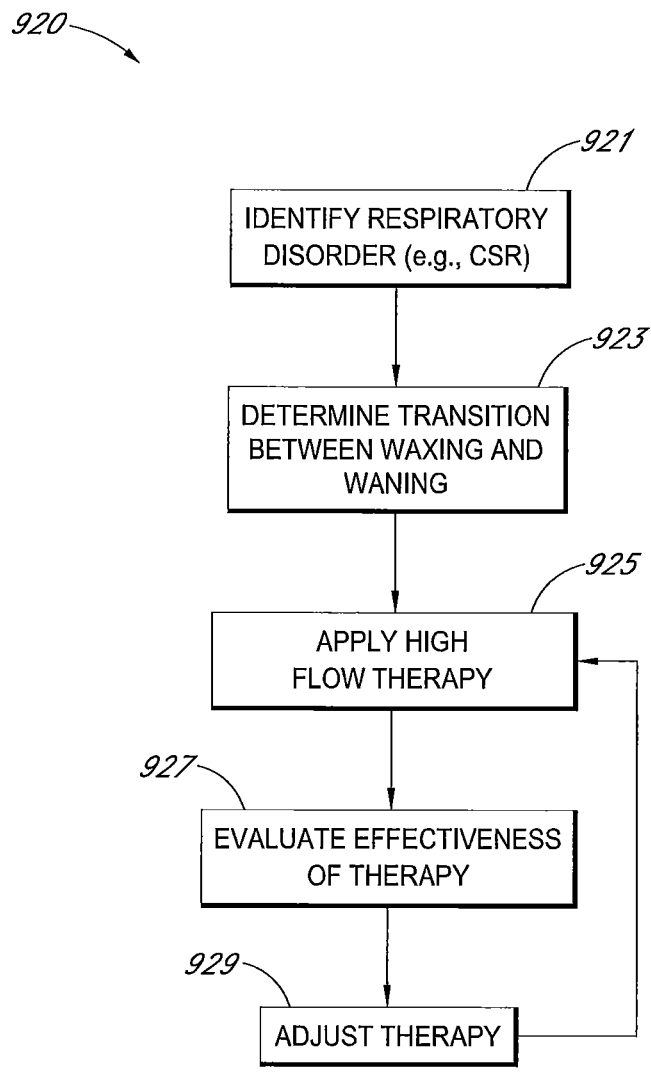
FIG. 9 illustrates a flow diagram of an embodiment of a high flow therapy treatment for respiratory disorders

FIG. 9 illustrates a flow diagram of an embodiment of a high flow therapy treatment for respiratory disorders, for example, including CSR. The therapy treatment process 920 begins by identifying a respiratory disorder, for example, CSR at 921. At 923, transitions between waxing and waning breath cycles are determined. At 925, therapeutic high flow therapy is applied. The high flow therapy can be applied as described elsewhere herein, including for example, applying high flow therapy between waxing and waning cycles, applying high flow therapy periodically or for a period of time or during transitions cycles, applying high flow therapy during exhalation, or according to a phase delay adjustment process as described in further detail below. At 927, the therapy effectiveness is evaluated. According to the evaluation, the therapy is adjusted at 929 and the therapy process returns to 925, where the therapeutic high flow therapy is again applied.

The phase delay is a time delay from when the controller detects a decrease or increase in the tidal flow of the patients breathing to when the controller increases or decreases the flow of gases delivered to the patient interface. In an embodiment, the phase delay tracks a delay period associated with the patient's chemoreceptors. Using the phase delay, the controller controls the magnitude of the flow delivered to the patient in an oscillatory fashion. The period of oscillation approximates the period of oscillation of the patients breathing, for example, between waxing and waning periods. In an embodiment, the shape of the oscillatory gas delivery waveform may track the shape of the oscillatory breathing waveform of the patient. In an embodiment, the peak flow delivered to the patient during the oscillatory flow profile may be adjusted using a scaling factor with respect to the measured difference between the maximum and minimum patient breathing tidal flows. In other embodiments, the peak flow can be a scaling factor from the maximum and/or minimum patient tidal flow. In an embodiment, the scaling factor can be constant throughout an entire cycle, or can be adjusted depending on whether the patient is in a waxing or waning period of the CSR cycle. For example, shallow breaths may require a certain flow while periods of hyperventilation may require a disproportionally different flow of therapy.

The phase delay applied by the controller may vary between about zero degrees and about three hundred and sixty degrees. The phase delay applied by the controller may vary between about zero degrees and about one hundred and eighty degrees. The phase delay applied by the controller may vary between about zero degrees and about ninety degrees. The phase delay applied by the controller may vary between about zero degrees and about forty five degrees. The phase delay applied by the controller may vary between about zero degrees and about two hundred and seventy degrees.

In some embodiments, the application or adjustment of high flow therapy is applied using a series of incremental phase delays or phase advancements based on the CSR cycle. For example, during an initial CSR cycle, high flow therapy is applied at a first time. The first time may be predetermined or it may be based on the identified CSR cycle and/or an observed chemoreceptor delay. During a subsequent CSR cycle, the high flow therapy is applied at a second time, which can be an incrementally advanced or delayed interval based on the CSR cycle. In other words, the second time is phase advanced or delayed from the first time. The amount of advancement or delay is based on the CSR cycle severity, the and/or based on the effect of previous high flow therapy applications. In an embodiment, after each CSR cycle, the effect of previous high flow therapy applications can be evaluated and optimal timing can be determined. The determination of phase delay application can be based on feedback from the patient. After a period of phase delays has been applied, the effect of the treatment on the patient is evaluated to determine if the phase delay is appropriate and is adjusted as needed in order to respond to the patient's reaction to the treatment. In an embodiment, the phase delay is periodically reevaluated in accordance with feedback from the patient.

Figure 10:
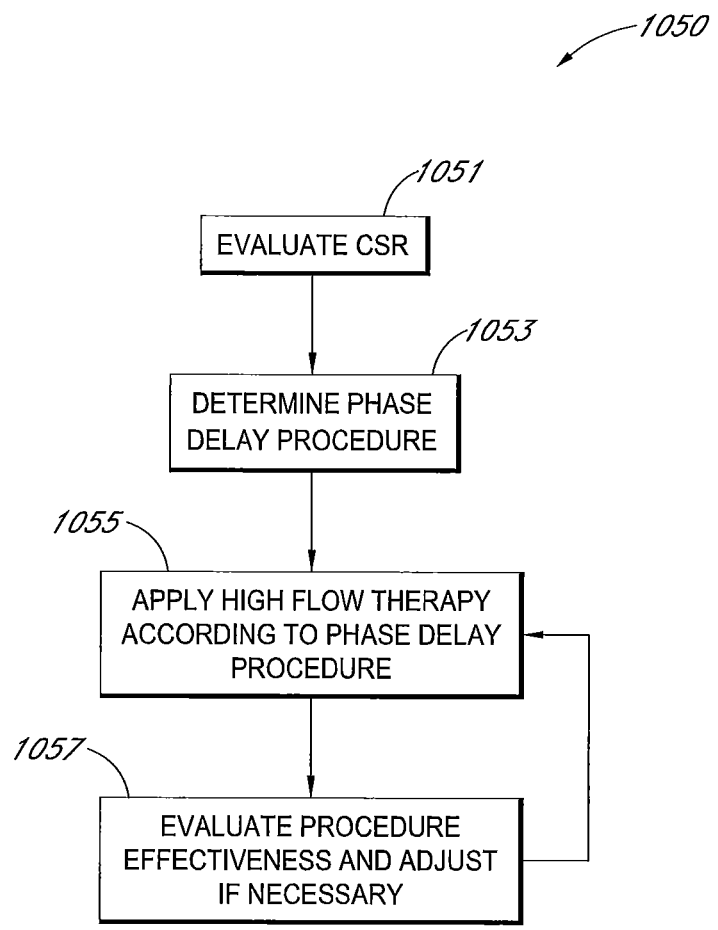
FIG. 10 illustrates a flow diagram of an embodiment of therapeutic high flow therapy application for treating CSR using a phase delay procedure.

In an embodiment, a pattern of incremental phase delays or advancements can be applied. For example, if it is determined that a particular delay is effective, the timing of the high flow therapy is determined and applied to gradually reduce the effects of CSR. In an embodiment, the system can apply a determined phase delay or advancement procedure over the course of multiple CSR cycles and then evaluate the data to refine high flow therapy application. In an embodiment, the system can apply a determined phase delay or advancement procedure over the course of a period of time, such as, for example, multiple nights or sessions. For example, in an embodiment, a first phase delay can be used for a first period of time and a second phase delay can be used for a second or subsequent period of time. In an embodiment, the phase delays can be part of a series of predetermined profiles. After multiple time periods, the effect of each phase delay is evaluated and the optimal delay is selected and implemented upon detection of future CSR cycles. FIG. 10 illustrates an embodiment of a phase delay procedure 1050 used to treat CSR cycles during high flow therapy. The procedure begins at 1051 where the patients CSR cycles are evaluated. At 1053, a phase delay procedure is determined based on the evaluation at 1051. At 1055, high flow therapy is applied according to the phase delay procedure determination at 1053. At 1057, after allowing the high flow therapy procedure to be applied for a period of time, the procedure's effectiveness is evaluated and adjusted as necessary. Once the evaluation at 1057 is completed, the procedure returns to the 1055 where high flow therapy is again applied according to the adjusted procedure of 1057

In some configurations, rather than adjusting flow rates, or in addition to adjusting flow rates, various mixtures of respiratory gases containing carbon dioxide and/or oxygen can be delivered from an external source with nasal high flow therapy, either continuously or periodically to control respiration. The addition of $CO_2$ or $O_2$ into a high flow therapy mixture of air allows the system to adjust $CO_2$ concentrations to help the body stabilize respiration. Thus, the addition of $CO_2$ or $O_2$ into the gas mixture can be periodically effected, in accordance with the principals discussed above, in order to allow the body to naturally regulate respiration.

In some configurations, the effects of a chosen therapy can be evaluated and/or controlled using an external monitor that can be connected to a flow generator, using pressure, flow or a combination of pressure and/or flow changes in the nasal cavity, in the interface or anywhere between the airways and the flow source. Such controls can be as described in detail in PCT Publication No. WO2013/172722, filed May 17, 2013, which is hereby incorporated by reference in its entirety.

As described above, in some embodiments, a hybrid mask can be used to treat CSR or other respiratory disorders. In an embodiment, the hybrid mask can be used as part of the CSR therapies described above, or it can be used independently of the therapies described above. As noted above, some embodiments of hybrid masks are described in PCT Publication WO2011/078703.

In an embodiment, a hybrid mask includes a nasal high flow component within a non-sealing mask. The mask can be a nasal and/or oral mask. The nasal high flow component directs a high flow of gas into the patient's nares. The high flow of gas is used to flush $CO_2$ from the patient's upper airway, including, for example, the patient's anatomical dead space, that may not me completely expired during expiration. The high flow of gas may optionally be heated and/or humidified.

Figure 11:
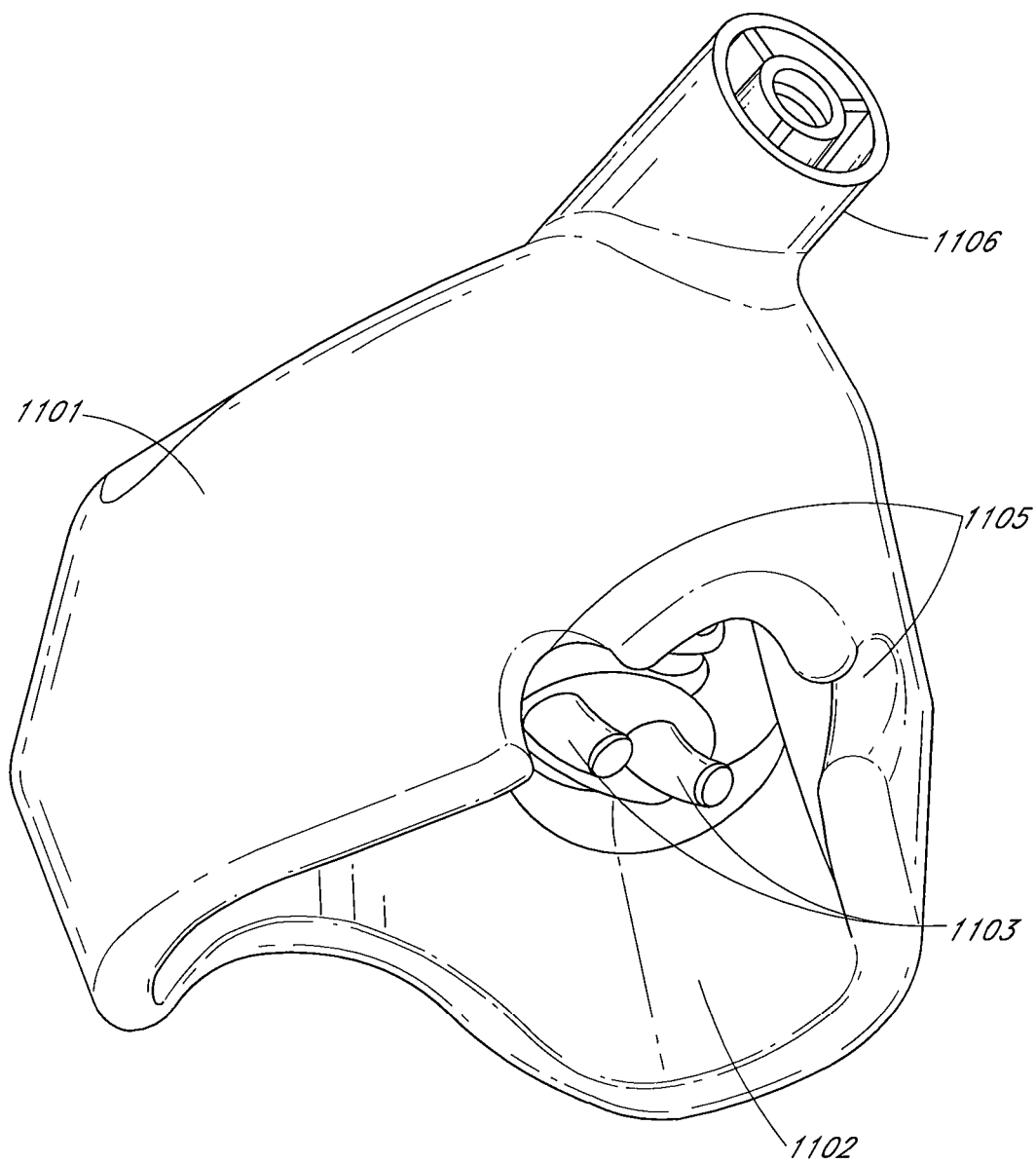
FIG. 11 illustrates an embodiment of a non-sealing mask useful to catching expired $CO_2$.

FIG. 11 illustrates an embodiment of a non-sealing mask 1101. The non-sealing mask portion is configured to contact the patient around the nose and/or mouth of the patient. For example, the mask can apply air flow to the nares using a conduit 1106 and/or prongs 1103. This mask portion creates a catchment 1102 that may collect expired $CO_2$. The nasal high flow can be adjusted or controlled to flush or remove $CO_2$ from the upper airway of the patient, as well as, or alternatively from only from, the catchment. As used herein, "non-sealing" is intended to mean that the mask is configured to capture expired gas, but not seal so much as to form a closed or sealed system. In this respect, the non-sealing mask should be able to allow gas from the nasal high flow to flow out of the mask without a significant increase in pressure to the patient that may inhibit expiration, yet still be capable of capturing expired $CO_2$ from expiration. This non-sealing may be obtained, for example, through additional bias flow holes 905 or by configuring portions of the mask to be spaced away from the patient's nose and/or mouth, for example as shown in FIG. 11.

The volume of a normal patient's nasal cavity portion of the anatomical dead space in the upper airway is generally about 50 mL. Thus, the volume of $CO_2$ collected within the nasal cavity is generally limited to approximately the same amount of $CO_2$. In the embodiment shown in FIG. 11, additional volume is provided which increases the volume of $CO_2$ which is capable of being captured. For example, the hybrid mask as depicted in FIG. 11 may provide as much as about 50 mL or more of additional volume. This allows for, for example, roughly double or more of the volume of $CO_2$ to be collected than would naturally occur without intervention in the patient's upper airway. In other embodiments, additional or larger catchments, as described in greater detail below, may be provided which allow for hundreds of mL of $CO_2$ to be captured. In an embodiment, the CO2 captured is in the range of 0 mL to 500 mL. In an embodiment, the range is about 25 mL to about 75 mL. In another embodiment, the range is about 100 mL to 200 mL. As would be understood by those of skill in the art, different sized catchments can be used in order to capture a desired amount of $CO_2$.

In this embodiment, when the nasal high flow is operating, $CO_2$ within the upper airway and the catchment is flushed or removed, or at least reduced. This allows the patient to breathe fresh air, in particular, during initial inspiration.

Alternatively, the nasal high flow may be reduced or stopped. This allows expired $CO_2$ to collect in the catchment for rebreathing. The catchment $CO_2$, along with $CO_2$ remaining in the upper airway causes $CO_2$ levels within the patient to increase. As such, in the presently described embodiment, the patient's $CO_2$ level can be controlled by high nasal flow. In particular, $CO_2$ level may be increased, when nasal high flow off or low, or decreased, when nasal high flow is on.

The presently described hybrid mask may be used in the treatment of CSR by controlling the amount of $CO_2$ available to the patient, thus controlling $CO_2$ levels within the patient. For example, during periods of heavy breathing (waxing), $CO_2$ levels within the patient typically reduce, as $CO_2$ is rapidly expired as a result of the heavy breathing. However, the presently described hybrid mask allows for $CO_2$ expired during heavy breathing (waxing) to be collected in the catchment. This allows for rebreathing of expired $CO_2$, thus increasing $CO_2$ during a period where $CO_2$ levels typically decrease.

Additionally, for example, during periods of reduced breathing (waning), nasal high flow may be used to flush $CO_2$ from within the upper airway (anatomical dead space) as well as within the catchment. As a result, less $CO_2$ is available to the patient, thus $CO_2$ levels decrease during a period where $CO_2$ levels within the patient typically increase.

Accordingly, by controlling the amount of $CO_2$ available to the patient by way of nasal high flow and/or the hybrid masks described herein, $CO_2$ levels of the patient may be controlled in order to trigger normal respiration. Further, the application of nasal high flow may be adjusted to incorporate any phase delays associated with chemoreceptors through the patient.

In an embodiment, in addition to or alternatively to using a mask as a $CO_2$ entrapment, a reservoir can be used to hold expired $CO_2$ or air enriched $CO_2$. For example, a container, such as, for example, an inflatable bag, hood or other similar container can be used to act as a reservoir to collect $CO_2$. In an embodiment, the container can be cleared from the expired air, expired air enriched by $CO_2$, or air enriched $CO_2$ either by an increase of nasal high flow and/or additional flow through the reservoir.

Although many of the above embodiments describe the application of high flow therapy, it is to be understood that this language can encompass both turning high therapy "on" from a zero flow applied state to a flow applied state as well as increasing a flow rate from a lower flow rate to a higher flow rate.

Conditional language, such as, among others, "can," "could," "might," or "may," unless specifically stated otherwise, or otherwise understood within the context as used, is generally intended to convey that certain embodiments include, while other embodiments do not include, certain features, elements and/or steps. Thus, such conditional language is not generally intended to imply that features, elements and/or steps are in any way required for one or more embodiments or that one or more embodiments necessarily include logic for deciding, with or without user input or prompting, whether these features, elements and/or steps are included or are to be performed in any particular embodiment.

Any process descriptions, elements, or blocks in the flow diagrams described herein and/or depicted in the attached figures should be understood as potentially representing modules, segments, or portions of code which include one or more executable instructions for implementing specific logical functions or steps in the process. Alternate implementations are included within the scope of the embodiments described herein in which elements or functions may be deleted, executed out of order from that shown or discussed, including substantially concurrently or in reverse order, depending on the functionality involved, as would be understood by those skilled in the art. It will further be appreciated that the data and/or components described above may be stored on a computer-readable medium and loaded into memory of the computing device using a drive mechanism associated with a computer readable storing the computer executable components such as a CD-ROM, DVD-ROM, memory stick, or network interface. Further, the component and/or data can be included in a single device or distributed in any manner. Accordingly, general purpose computing devices may be configured to implement the processes, algorithms and methodology of the present disclosure with the processing and/or execution of the various data and/or components described above.

Although the present invention has been described in terms of certain embodiments, other embodiments apparent to those of ordinary skill in the art also are within the scope of this invention. Thus, various changes and modifications may be made without departing from the spirit and scope of the invention. For instance, various components may be repositioned as desired. Moreover, not all of the features, aspects and advantages are necessarily required to practice the present invention. Accordingly, the scope of the present invention is intended to be defined only by the claims that follow.

What is claimed is:

1. A high flow respiratory assistance system comprising:
   a flow source configured to provide a high flow of respiratory gases in order to administer high flow therapy;
   a non-sealing interface which prevents a significant increase in pressure, the non-sealing interface in fluid communication with the flow source and providing the high flow of respiratory gases in order to clear $CO_2$ from anatomical dead space;
   a sensor configured to sense an indication of a respiration and generate a respiration signal;
   a controller, wherein the controller:
      receives the respiration signal from the sensor,
      identifies respiration criteria based on the respiration signal, and
      controls the flow of gases by varying a target flow rate to deliver nasal high flow based on the identification of the respiration criteria, the control of the flow of gases at the variable target flow rate configured to aid stabilization of respiration by increasing or decreasing the flow rate to change the amount of $CO_2$ cleared from the anatomical dead space.

2. The system of claim 1, further comprising a humidifier in fluid communication with and between the flow source and the interface.

3. The system of claim 1, wherein the controller identifies respiration criteria by analysing an amplitude of the respiration signal for shallow breathing, apneas, heavy breathing, or hyperventilation.

4. The system of claim 1, wherein the controller identifies respiration criteria by analysing the respiration signal for periods of a waxing respiration portion and a waning respiration portion.

5. The system of claim 1, wherein the controller controls the flow of gas by applying the high flow of respiratory gases during a transition between the waxing portion and the waning portion.

6. The system of claim 1, wherein the respiration criteria is a period and phases of the respiration signal.

7. The system of claim 6, wherein the controller initiates nasal high flow during at least one of the phases.

8. The system of claim 6, wherein the controller identifies a phase delay associated with chemoreceptor signals.

9. The system of claim 8, wherein the controller initiates nasal high flow based at least in part on the phase delay.

10. The system of claim 3, wherein the controller determines the respiratory criteria is indicative of Cheyne-Stokes Respiration.

11. The system of claim 10, wherein the controller determines a periodic signal amplitude having a 90% reduction for 10 seconds or more of a normal signal amplitude is indicative of Cheyne-Stokes Respiration.

12. The system of claim 3, wherein the controller determines a periodic signal amplitude having a 50% reduction from a normal signal amplitude is indicative of Cheyne-Stokes Respiration.

13. The system of claim 12, wherein the controller determines a periodic signal amplitude having a 50% reduction for 10 seconds or more of a normal signal amplitude is indicative of Cheyne-Stokes Respiration.

14. The system of claim 1, wherein the flow source provides a high flow of respiratory gases of greater than 40 litres per minute.

15. The system of claim 1, wherein the non-sealing interface is a nasal cannula.

16. The system of claim 1, wherein the controller applies the flow of gas for a window of time less than or approximately equal to a period of a Cheyne-Stokes Respiration cycle.

17. A high flow respiratory assistance system comprising:
    a flow source configured to provide a high flow of respiratory gases in order to administer high flow therapy;
    a non-sealing interface which prevents a increase in pressure significant enough to inhibit expiration, the non-sealing interface in fluid communication with the flow source and providing the high flow of respiratory gases to in order to clear expiratory gases from an airway;
    a sensor configured to sense an indication of flow, the indication of flow usable to determine a respiration;
    a controller, wherein the controller:
       receives the indication of flow and determines a respiration signal from the sensor,
       identifies respiration criteria based on the respiration signal, and
       controls the flow of gases by varying a target flow rate to deliver nasal high flow based on the identification of the respiration criteria, the control of the flow of gases at the variable target flow rate configured to aid stabilization of respiration by increasing or decreasing the flow rate to change the amount of $CO_2$ cleared from the anatomical dead space.

18. The system of claim 17, wherein the expiratory gases comprise exhaled CO2 that is not fully exhaled from the airway.

19. The system of claim 17, wherein assisting respiration comprises stabilizing respiration.

20. The system of claim 17, wherein assisting respiration comprises lowering a flow rate when hyperventilation is detected.

21. The system of claim 17, wherein the airway is an anatomical dead space.

* * * * *